United States Patent
Zubairy et al.

(10) Patent No.: US 10,317,342 B2
(45) Date of Patent: Jun. 11, 2019

(54) NANOMETER SCALE MICROSCOPY VIA GRAPHENE PLASMONS

(71) Applicant: The Texas A&M University System, College Station, TX (US)

(72) Inventors: Muhammad Suhail Zubairy, College Station, TX (US); Mohammad D. Al-Amri, Riyadh (SA); Xiaodong Zeng, College Station, TX (US)

(73) Assignees: The Texas A&M University System, College Station, TX (US); The National Centre for Applied Physics, KACST, Riyadh (SA)

( * ) Notice: Subject to any disclaimer, the term of this patent is extended or adjusted under 35 U.S.C. 154(b) by 135 days.

(21) Appl. No.: 15/200,178

(22) Filed: Jul. 1, 2016

(65) Prior Publication Data

US 2017/0003223 A1 Jan. 5, 2017

Related U.S. Application Data

(60) Provisional application No. 62/188,710, filed on Jul. 5, 2015.

(51) Int. Cl.
| | | |
|---|---|---|
| G02B 21/00 | (2006.01) | |
| G01N 21/64 | (2006.01) | |
| G02B 21/16 | (2006.01) | |
| G02B 21/36 | (2006.01) | |
| G02B 21/06 | (2006.01) | |

(52) U.S. Cl.
CPC ....... *G01N 21/648* (2013.01); *G01N 21/6458* (2013.01); *G02B 21/06* (2013.01); *G02B 21/16* (2013.01); *G02B 21/361* (2013.01); *G02B 21/365* (2013.01)

(58) Field of Classification Search
USPC ............................................. 348/78; 382/141
See application file for complete search history.

(56) References Cited

U.S. PATENT DOCUMENTS

| | | | | |
|---|---|---|---|---|
| 2009/0066963 A1* | 3/2009 | Petek | ...................... | G01B 9/04 |
| | | | | 356/450 |
| 2014/0131574 A1* | 5/2014 | Zewail | .................... | H01J 37/26 |
| | | | | 250/307 |
| 2014/0376799 A1* | 12/2014 | Wang | ........................ | G01J 3/42 |
| | | | | 382/141 |
| 2015/0372159 A1* | 12/2015 | Englund | ................. | H01L 31/09 |
| | | | | 356/328 |

(Continued)

OTHER PUBLICATIONS

E. Betzig, et al. "Imaging Intracellular Fluorescent Proteins at Nanometer Resolution", Science 313,1642 (2006).

(Continued)

*Primary Examiner* — Chikaodili E Anyikire
(74) *Attorney, Agent, or Firm* — Saliwanchik, Lloyd & Eisenschenk

(57) ABSTRACT

Novel and advantageous systems and methods for performing nanometer-scale microscopy using graphene plasmons (GPs) are provided. Sub-diffraction microscopy can be achieved, taking advantage of the extremely small plasmon wavelength and low dissipation of GPs. Nanometer-scale resolution can be obtained under very weak light intensity, which is especially important in the imaging of biological systems.

11 Claims, 7 Drawing Sheets

(56) References Cited

U.S. PATENT DOCUMENTS

2016/0227639 A1* 8/2016 Kaminer .................. H05G 2/00

OTHER PUBLICATIONS

C. Hettich, et al. Science 298, 385 (2002).
Z. Y. Liao, et al. Phys. Rev. A 85, 023810 (2012).
J. T. Chang, et al. "Measurement of the separation between atoms beyond diffraction limit", Phys. Rev. A 73 031803 (R) (2006).
J. T. Chang, et al. Phys. Rev.; A 74, 04382, (2006).
S. Qamar, et al., "Atom microscopy via two-photon spontaneous emission spectroscopy," Phys. Rev A 79, 043814 (2009).
H. B. Li, et al, "Optical imaging beyond the diffraction limit via dark states," Phys. Rev. A 78, 013803 (2008).
M. J. Rust, et al., "Stochastic optical reconstruction microscopy (STORM) provides sub-diffraction-limit image resolution," Nat. Methods 3, 793 (2006).
Z. Liu, et al. "Far-Field Optical Hyperlens Magnifying Sub-Diffraction-Limited Objects," Science 315, 1686 (2007).
V. Westphal, et al. "Nanoscale Resolution in the Focal Plane of an Optical Microscope", Phys. Rev Lett. 94, 143903 (2005).
D. Wildanger, et al. "Diffraction Unlimited All-Optical Recording of Electron Spin Resonances," Phys. Rev.Lett 107, 17601 2011.
T. A. Klar, et al. "Fluorescence microscopy with diffraction resolution barrier broken by stimulated emission," Proc. Science Natl. Acad. Sci. USA 97, 8206 (2000).
M.G. L. Gustafsson, "Surpassing the lateral resolution limit by a factor of two using structured illumination microscopy," J Microsoft, 198, 82 (2000).
J. T. Frohn, et al. "True optical resolution beyond the Rayleigh limit achieved by standing wave illumination", Proc. Natl. Acad. Sci. USA 97, 7232(2000).
R. Heintzmann, et al. "Saturated patterned excitation microscopy—concept for optical resolution improvement," Opt. Soc. Am. A USA, col. 19, No. 8, 1599 (2002).
M.G. L. Gustafsson, "Nonlinear structured-illumination microscopy: Wide-field fluorescence imaging with theoretically unlimited resolution," Proc. Natl. Acad. Sci USA 102, 13081 (2005).
F. Wei, et al. "Plasmonic Structured Illumination Microscopy," Nano Lett. 10, 2531 (2010).
A. K. Geim, et al "The rise of graphene," Nature Matter, 6 183, (2007).
A. H. Castro, et al. "The electronic properties of graphene," Rev. Mod. Phys. 81, 109 (2009).
R. R. Nair, et al. "Fine Structure Constant Defines Visual Transparency of Graphene," Science 320, 1308 (2008).
J. Chen, et al. "Optical nano-imaging of gate-tunable graphene plasmons," Nature 487, 77 (2012).
Z. Fei, et al."Gate-tuning of graphene plasmons revealed by infrared nano-imaging," Nature 487, 82 (2012).
Z. Fang, et al. "Gated Tunability and Hybridization of Localized Plasmons in Nanostructured Graphene," ACS Nano 7, 2388 (2013).
T. Low, et al. "Graphene Plasmonics for Terahertz to Mid-Infrared Applications," ACS Nano 8, 1086 (2014).
L. Ju, et al. "Graphene plasmonics for tunable terahertz metamaterials," Natl. Nanotechnology, 6, 630 (2011).
M. Gullans, et al. "Single-Photon Nonlinear Optics with Graphene Plasmons," Phys. Rev. Lett. 111, 247401 (2013).
A. N. Grigorenko, et al. "Graphene plasmonics," Nat. Photonics, 6, 749 (2012).
A. Vaki,et al, "Transformation Optics Using Graphene" Science 332, 1291 (2011).
T. R. Zhan, et al. "Band Structure of plasmons and optical absorption enhancement in graphene on subwavelength dielectric gratings at infrared frequencies" Phys Rev. B 86, 165416 (2012).
B. Wunsch, et al "Dynamical polarization of graphene at finite doping", New J. Phy. 8, 318 (2006).
E. H. Hwang, et al. "Dielectric function, screening, and plasmons in 2D graphene," Phys. Rev. B 75, 205418 (2007).
S. A. Mikhailov, et al. "A new electromagnetic mode in graphene," Phys.Rev. Lett. 99, 016083, (2007).
M. Jablan, et al. "Plasmonics in graphene at infrared frequencies," C, Phys. Rev. B 80, 245435 (2009).
F. H. L. Koppens, et al. "Graphene Plasmonics: A Platform for Strong Light-Matter Interactions," Nano Lett. 11, 3370 (2011).
X. H. Yao, et al. Phys. Rev. Lett. 112, 055501 (2014).
B. Wang, et al. "Strong Coupling of Surface Plasmon Polaritons in Monolayer Graphene Sheet Arrays", Phys. Rev. Lett. 109, 073901 (2012).
F. Balzarotti, et al. "Plasmonics Meets Far-Field Optical Nanoscopy", ACS Nano 6, 4580 (2012).
B. Gjonaj, et al. "Focusing and Scanning Microscopy with Propagating Surface Plasmons," Phys. Rev. Lett. 110, 266804 (2013).

* cited by examiner

NANOMETER SCALE MICROSCOPY VIA GRAPHENE PLASMONS

CROSS-REFERENCE TO A RELATED APPLICATION

This application claims the benefit of U.S. Provisional Application Ser. No. 62/188,710, filed Jul. 5, 2015, which is hereby incorporated by reference in its entirety.

BACKGROUND OF INVENTION

The classical Abbe diffraction limit in fluorescence light microscopy had been a barrier for obtaining image information with a resolution better than half the wavelength of light for quite a long time. As the frontiers of science and technology approach the nanoscale, defeating the diffraction limit is a prerequisite to get nanometer resolution, especially in for biological samples. Several recent methods are capable of resolving structure beyond the diffraction limit, but these sub-diffraction techniques suffer from shortcomings. For example, photoactivated localization microscopy and stochastic optical reconstruction microscopy methods of localizing individual fluorophores in the sample to sub-diffraction precision require the generation of a large amount of raw images. Also, stimulated-emission depletion requires a sub-diffraction illumination of light and spot-by-spot scanning of the sample, which leads to low speed and requires a strong driving laser field.

Another high-resolution method, structured illumination microscopy (SIM), has been of special interest in recent years. Linear SIM was previously realized with resolution limitation, but more recently nonlinear SIM has become a widely used method to get a high-resolution image. In nonlinear SIM, two counter-propagating fields construct a spatially periodic illumination structure. The atoms or molecules have different fluorescence abilities under different light intensities. This dependence is nonlinear rather than the atom or molecule undergoing the multiphoton's process; in practice, the nonlinear order is less than four. This generates high spatial frequency information in the far field, hence leading to higher resolution. However, high resolution means higher-order nonlinearity and subsequently high light intensity. This leads to the possibility for damage to the sample and thus limits the use of this kind of microscopy, especially in biological systems. Wei et al. (*Nano Lett.*, 10, 2531, 2010) use metal plasmons to construct a periodical strip pattern in a microscopy method called plasmon structure-illumination microscopy. However, due to the limitations of metal plasmons, this method has poor resolution and low precision.

BRIEF SUMMARY

Embodiments of the subject invention provide novel and advantageous systems and methods for performing nanometer-scale microscopy using graphene plasmons (GPs). Sub-diffraction microscopy can be achieved, taking advantage of the extremely small plasmon wavelength and low dissipation of GPs. Nanometer-scale resolution can be obtained under very weak light intensity, which is especially important in the imaging of biological systems.

In an embodiment, a method of performing nanometer-scale microscopy on a sample can comprise: providing the sample to an imaging system comprising a graphene layer, wherein the sample is disposed over the graphene layer; exciting a plurality of GPs in the graphene layer as an illumination source for imaging the sample; and capturing an image of the sample using the GPs as the illumination source.

In another embodiment, a system performing nanometer-scale microscopy on a sample can comprise: a substrate; a graphene layer disposed on the substrate; a dielectric layer disposed on the graphene layer and configured to have the sample disposed thereon; and a lens positioned above the dielectric layer. The system can be configured to perform imaging by exciting a plurality of GPs in the graphene layer as an illumination source for imaging the sample, and using the lens to capture an image of the sample using the GPs as the illumination source.

DETAILED DISCLOSURE

Figure 1A:
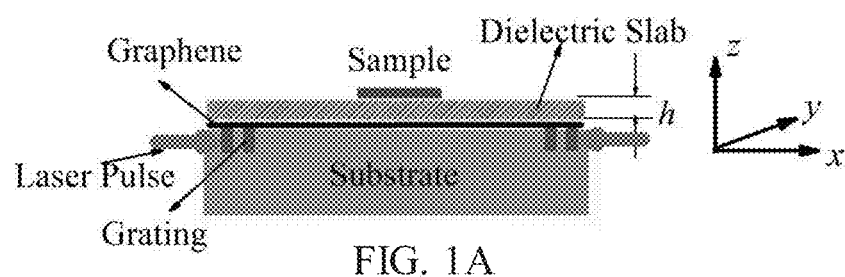
FIG. 1A shows a sectional view of a system according to an embodiment of the subject invention.

Embodiments of the subject invention provide novel and advantageous systems and methods for performing nanometer-scale microscopy using graphene plasmons (GPs). Sub-diffraction microscopy can be achieved, taking advantage of the extremely small plasmon wavelength and low dissipation of GPs. Nanometer-scale resolution can be obtained under very weak light intensity, which is especially important in the imaging of biological systems. In an embodiment, a system can include a substrate, a layer of graphene (e.g., a monolayer of graphene) disposed on the substrate, and a layer of dielectric material disposed on the graphene layer. The sample to be viewed can be disposed on the dielectric layer that is on the graphene layer, and a lens (e.g., an objective lens) can be used to capture one or more images. GPs can be excited and can provide illumination of the sample for imaging. The thickness of the dielectric layer disposed on the graphene layer can be selected or tuned to provide optimum results.

Graphene, a single layer of carbon atoms arranged in a honeycomb lattice, has advantageous and unique electronic, mechanical, and optical properties. The linear dispersion relation near the Dirac point of the energy band induces a special optical response to light, including high efficiency for light-matter interactions, strong optical nonlinearity, and unusual surface plasmons. GPs have advantageous properties, including frequency region, tunability, long life (compared to other types of plasmons), and extreme light confinements. The Fermi velocity of doped graphene is $v_F=106$ m/s, which leads to a wave number that is about two orders of magnitude larger than that in vacuum. Additionally, due to Pauli blocking, doped graphene has a low absorption in the mid-infrared region. Embodiments of the subject invention make use of these advantageous properties of graphene to perform structured-illumination microscopy using GPs as the illumination light. In such a system, the effective illuminated field frequency can be large even though the real frequency $\omega$ is in the mid-infrared region. By exploiting the weak-field intensity associated with linearity, very large spatial frequency can be mixed to the far field, and an increase of more than a hundred times resolution can be achieved.

In the long wavelength and high doping limit—i.e., $\hbar\omega \ll E_F$, where $E_F$ is the Fermi energy and $\hbar$ is the reduced Planck constant (which is the Planck constant ($6.626\times10^{-34}$ J·s) divided by $2\pi$)—the in-plane conductivity of graphene can be described by a simple semi-classical local Drude model $\sigma(\omega)=ie^2E_F/[\pi\hbar-(\omega+i/\tau)]$ under the random-phase approximation. Here, $\tau$ describes the momentum relaxation time due to impurity or phonon-, 2 mediated scattering. In the special frequency region, it can be expressed as $\tau=\mu E_F/ev^2_F$ where $\mu$ is the mobility of the graphene charge carriers. The tunability of the graphene results from the controllability of the Fermi energy, such as by adjusting the temperature or electrostatic gating.

Similar to normal metals having collective oscillation of free electrons, the electron carriers of doped graphene can also respond to an electromagnetic field resonantly leading to GPs. For a plane dielectric—monolayer graphene—dielectric model, the plasmon dispersion relation has the following form:

$$k_{gp}(\omega) \approx \frac{2\pi\hbar^2\varepsilon_0(\varepsilon_1+\varepsilon_2)}{2e^2E_F}\omega^2(1+i/\tau\omega) \quad (1)$$

$$\approx \frac{(\varepsilon_1+\varepsilon_2)}{4\alpha}\frac{\omega}{\omega_F}k_0(1+i/\tau\omega).$$

where $\alpha=e^2/4\pi\hbar\varepsilon_0 c\approx 1/137$ is the fine-structure constant and $\omega_F=E_F/\hbar$, and $k_0$ is the vacuum wave number. Here $\varepsilon_1$ and $\varepsilon_2$ are the dielectric permittivity above (i.e., closer to the sample) and below (i.e., farther away from the sample) the graphene, respectively. The wave number is about two orders of magnitude larger than the vacuum wave number and can lead to extremely large sub-diffraction capability.

The spatial density of the sample atoms can be decomposed into its spatial Fourier components, $$F(x,y)=\iint f(k_x,k_y)e^{ik_x x+ik_y y}dk_x dk_y. \quad (2)$$

As in incoherent fluorescence microscopy, the measured image M(x, y) can be described by a multiplication of the local excitation intensity I (x, y) by the local fluorescence concentration F(x,y), followed by a convolution with the point-spread function T (x, y) of the incoherent imaging system for the emitted field, $$M(x,y)=\iint [F(x',y')P(x',y')]T(x-x',y-y')dk'dy', \quad (3)$$

where P(x'.y')=AI(x', y') is the fluorescence ability or population of the excited state. Here, A is a constant and dependent on the characteristics of the atom. In the spatial frequency domain, the image reads $m(k_x,k_y)=t(k_x, k_y)\phi(k_x, k_y)$, where $m(k_x,k_y)$ and $t(k_x,k_y)$ are the corresponding two-dimensional Fourier transformations of M(x,y) and T(x,y). The function $t(k_x,k_y)$ is also called the optical transfer function (OTF). Here, $\phi(k_x,k_y)$ is the spatial frequency spectrum.

Figure 2A:
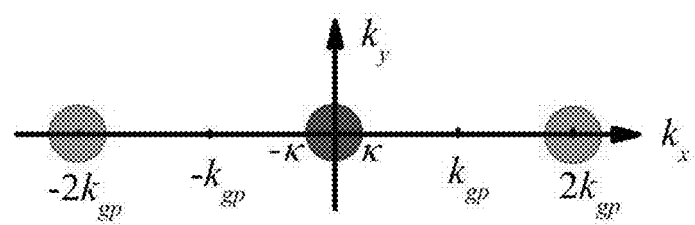
FIG. 2A shows a diagram of spatial frequency. The circle at the origin (in the middle of FIG. 2A) contributes to the conventional microscopy. The circles on the left and the right, having a center at ±2 $k_{gp}$ correspond to the linear response of the illumination pattern.

In conventional fluorescence microscopy, only the Fourier components within the passband $\sqrt{k^2_x+k^2_y}=k_\parallel \leq 2$ NA $k_0=\kappa$ can be observed as the OTF is nonzero only in this region. Here, NA is the numerical aperture. Referring to FIG. 2A, only the spatial frequencies inside the circle with the center at the origin would contribute to the image in such a case. Traditional linear structured illumination microscopy (SIM) uses a structured-illumination pattern and utilizes the so-called "moiré effect" to couple some of the high spatial frequency information from outside of the circle into the circle to improve the resolution. If the illumination field intensity pattern is sinusoidal with period the spatial frequency spectrum has the following form:

$$\phi(k_x,k_y)=2f(k_x,k_y)+f(k_x-k_1,k_y)e^{i\Delta_x}+f(k_x+k_1,k_y)e^{-\Delta_x}. \quad (4)$$

where $k_1=2\pi/\lambda_1$ and $\Delta_x$ is the shift of the pattern. Because of the diffraction limit, $\lambda_1$ cannot be smaller than $\lambda_0/2$. The spatial frequency region is enlarged to a circle with radius $K+k_1$. In an actual experiment, the objective lens can sometimes be used as the illumination source. The wave number $k_1$ is approximately equal to K, and the resolution can be extended by a factor of 2.

In the example discussed below, a sample used was similar to that in Heintzmann μ. (*J. Opt. Soc. Am. A.*, 19, 1599, 2002) and Gustafsson (*Proc. Natl. Acad. Sci.*, USA, 102, 13081, 2005), both of which are hereby incorporated herein by reference in their entireties. In Heintzmann et al. and Gustafsson et al., the saturated excitation probability P of the fluorescence atom in Equation (3) is given by $P=1-\Gamma/(\eta 1+\Gamma)$, where $\eta$ is the absorption crossing section and $\Gamma$ is the decay rate of the atom. It is clear that the fluorescence is nonlinearly dependent on the illumination light intensity with period $\lambda_1$ if a large $\eta$ and a small $\Gamma$ are chosen. The Taylor expansion contains infinite terms; however, only the first several terms can overcome the noise. In vacuum, because of the diffraction effect, the $m^{th}$-order expansion at most can mix the $mk_1$ spatial frequency to the far field. For a given atom, in order to increase the nonlinear effect, the field must be very strong, which can be potentially harmful to the sample.

In many embodiments of the subject invention, graphene (e.g., monolayer graphene) can be used for high-resolution microscopy with a very weak field, thereby inhibiting potential harm to the sample. Linear response is focused on herein, and high-order nonlinearity is not discussed at length.

Figure 1B:
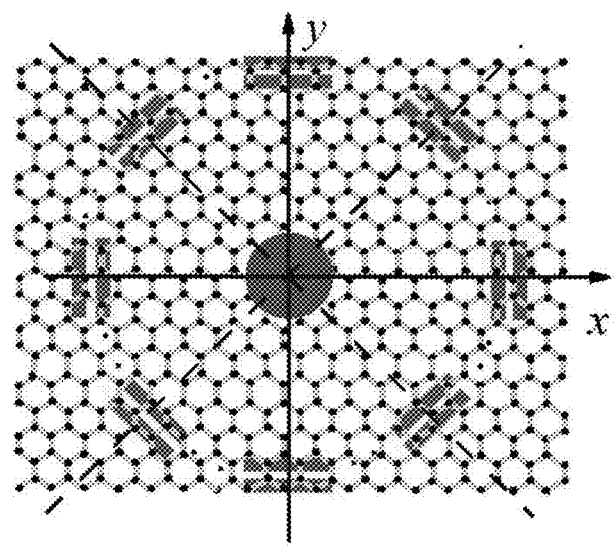
FIG. 1B shows a top view (with some layers appearing transparent for depiction purposes) of a portion of the system shown in FIG. 1A.

Referring to FIGS. 1A and 1B, in an embodiment, a system can include a substrate, a layer of graphene (e.g., a monolayer of graphene) disposed on the substrate, and a layer of dielectric material (labeled "dielectric slab in FIG.

1A) disposed on the graphene layer. The sample to be viewed can be disposed on the dielectric layer that is on the graphene layer, and a lens (e.g., an objective lens, as depicted in FIG. 1A) can be used to capture an image. Because the intensity of the GPs from the graphene layer decreases exponentially as the distance from the graphene increases, the electromagnetic field intensity on the sample can be manipulated by optimizing the thickness h of the dielectric layer. The substrate can include dielectric gratings, which can be curved (e.g., circular) distributions around the sample position; the gratings can be seen in FIGS. 1A and 1B, the latter of which is a top view of the sample (the circle in the middle), the graphene layer (the hexagons), and the dielectric gratings (the plurality of double lines forming a circle around the sample).

In an embodiment, two laser pulses can irradiate the gratings to excite two plasmons. In alternative embodiments, other methods can be used to generate plasmons, such as the methods described in Yao et al. (*Phys. Rev. Lett.,* 112, 05501, 2014), which is hereby incorporated herein by reference in its entirety. The two plasmons with the same wave number have different propagation directions and can construct a periodic pattern in one dimension. A plasmon can propagate and be reflected by the gratings on the opposite side and can affect the field pattern. However, the coupling between the plasmon and the reflection plasmon may be weak due to wave-vector mismatching. Additionally, the dissipation of the GPs can also decrease the reflection plasmon intensity. Because of these factors, the reflection plasmon affects the field pattern only slightly.

Figure 1C:
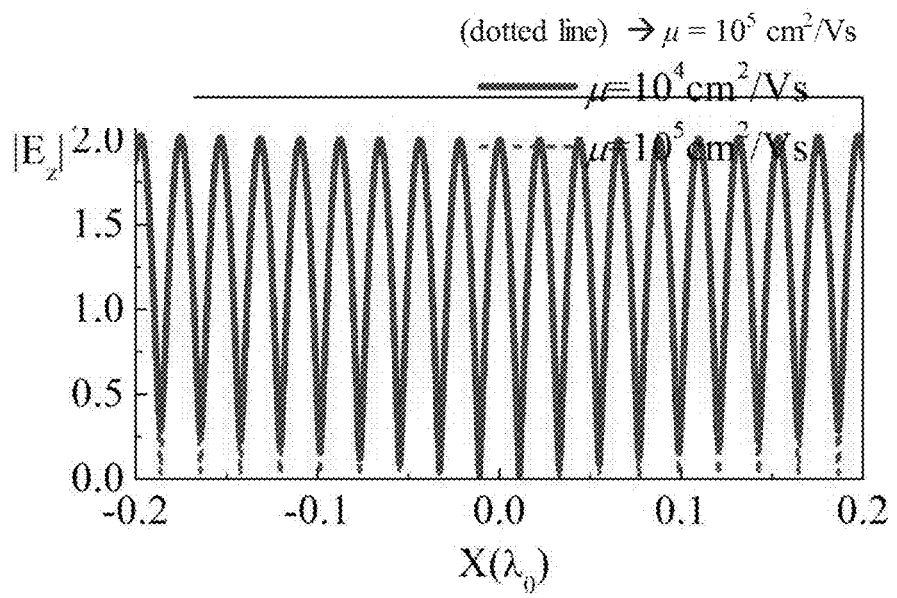
FIG. 1C shows a plot of light intensity along the x-axis for two different values of graphene charge carrier mobility ($\mu=10^4$ cm$^2$V$^{-1}$s$^{-1}$—solid line, and $10^5$ cm$^2$V$^{-1}$s$^{-1}$—dotted line). The other parameters are $E_f=0.6$, $\hbar\omega=0.2$ eV, and $\varepsilon_1=\varepsilon_2=2$. At point x=0, the two plasmons have the same field amplitude.

FIG. 1C shows a plot of light intensity along the x-axis for different μ values when the two counter-propagation plasmons are along the x-direction. The real parts of the wave numbers are about 45.7 $k_0$ with a corresponding wavelength of $\lambda_{gp}=0.0219\lambda_0$, which is very small compared to that in vacuum. The imaginary parts are 0.246 $k_0$ and 0.025 $k_0$ for $\mu=10^4$ cm$^2$V$^{-1}$s$^{-1}$ and $\mu=10^5$ cm$^2$V$^{-1}$s$^{-1}$, respectively, which induce decreases in the plasmon intensity as the plasmon propagates. At the location of the sample, the field intensity pattern along the x-axis is almost sinusoidal due to Im($k_{gp}$), which is much smaller than Re($k_{gp}$).

Figure 2B:
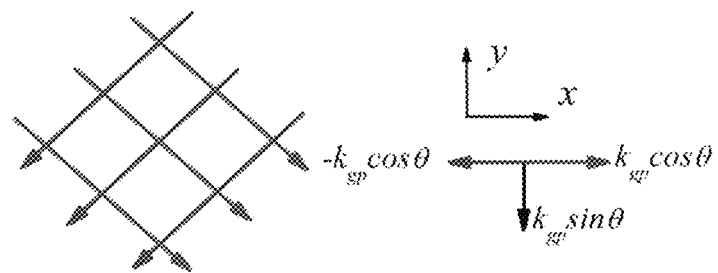
FIG. 2B shows a diagram representing control of the directions of two graphene plasmons (GPs). A sinusoidal pattern with effective wave number $k_{gp}$ cos θ can be constructed.

Comparing with the theory in Wei et al. (*Nano Lett.,* 10, 2531, 2010), which is hereby incorporated herein by reference in its entirety, for the linear response, the emitted field contains the information of the ±2 $k_{gp}$ and 0 $k_0$ components shown in FIG. 2A. Using the phase-shift method, the components can be separated. In this step, the initial phase of one incident pulse can be changed to manipulate the location of the illumination pattern. If just linear effect is used, the pattern can be moved three times to get three images. However, with only this information, the distribution of the atom cannot be fully reconstructed. In order to obtain the residual Fourier information in the x-direction, the direction of the two illumination pulses can be controlled, as shown in FIG. 2B. This will construct a sinusoidal field pattern in the x-axis direction with an effective period of $\pi/k_{gp}\cos\theta$, where θ is the angle between the plasmons and the x-axis. By controlling θ, all the information along the x-axis can be extracted. Similarly, all the Fourier components in Equation (2) can be obtained with $k_i \leq 2 k_{gp}+\kappa$ by rotating the x-axis around the origin.

Figure 5A:
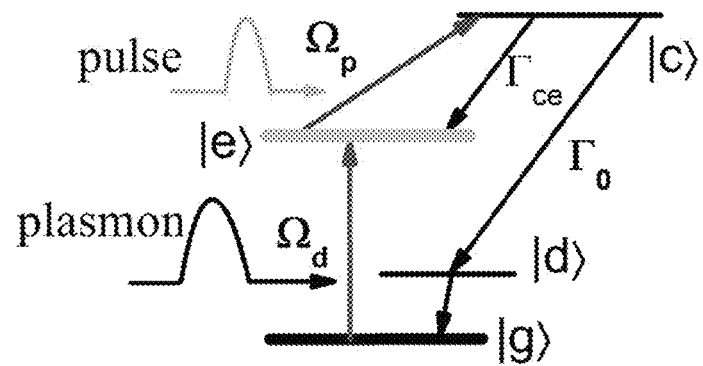
FIG. 5A shows a diagram representing a sample atom structure. The atom can decay from level |c> to |e> and |d> spontaneously with decay rates $\Gamma_{ce}$ and $\Gamma_0$, respectively.
Figure 5B:
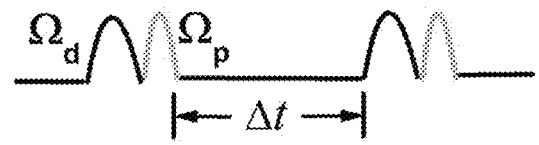
FIG. 5B shows a diagram representing the concept of two pulses irradiating a sample periodically.

The pulse length of the GPs can be chosen to maximize the quality of the resulting image. For example, the pulse length can be 1 nanosecond (ns) or on the order of 1 ns (i.e., from 1 ns to 9 ns), and the separation between two pulses can be 30 ns or on the order of 10 ns (i.e., from 10 ns-99 ns). FIG. 5*b* demonstrates this concept. A pulse separation of 30 ns is long enough to bring the atom back to the ground state. The photon collection efficiency can be, for example, between 0.1 and 1.0. If a photon collection efficiency of 0.1 is assumed with a pulse length of 1 ns and a pulse separation of 30 ns, then $3\times10^6$ photons can be collected from one atom in 1 second, on average. To obtain the image shown in FIG. 3C, about 10,000-15,000 images are required. Factoring in the time for controlling the pulse phase and direction, a process to obtain 10,000 to 15,000 images can take on the order of tens of seconds to minutes, which is similar to conventional SIM.

Compared to GPs, surface plasmons based on a metal film have symmetry and anti-symmetry eigenmodes. The symmetry mode has a small wave number associated with low-resolution ability, and the anti-symmetry mode has a relatively large wave number. However, this mode can have large dissipation, which is harmful to be used in imaging. As a result, use of GPs as discussed herein is advantageous.

Systems and methods of embodiments of the subject invention can provide image resolution of 100 nm or less. For example, a resolution of 10 nm or about 10 nm can be achieved.

Embodiments of the subject invention include linear schemes for sub-diffraction microscopy by using GPs, taking advantage of the extremely small plasmon wavelength and low dissipation of GPs. An image with nanometer-scale resolution can be obtained under very weak light intensity, which is especially important in the imaging of biological systems. The height of the sample can lead to some limitations, and embodiments of the subject invention can be most advantageous with samples having a height in of less than 100 nanometers (nm). Systems of embodiments of the subject invention are particularly powerful when analyzing biological molecular structures. The related art SIM technique does not consider dipole-dipole interactions and, if the fluorescence atoms are too close (i.e., about 10 nm), the atoms can affect each other.

Embodiments of the subject invention use GPs for nanometer-scale microscopy. The scheme takes advantage of the extremely large wave number of GPs and the low loss of graphene. Unlike conventional nonlinear SIM based on high-order nonlinearity associated with high intensity light, the methods and systems described herein only require linear response. Consequently, only a very weak field is needed, which means less damage to the sample, thereby leading to advantageous imaging of delicate samples, particularly biological systems and samples.

The methods and processes described herein can be embodied as code and/or data. The software code and data described herein can be stored on one or more computer-readable media, which may include any device or medium that can store code and/or data for use by a computer system. When a computer system reads and executes the code and/or data stored on a computer-readable medium, the computer system performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that is capable of storing computer-readable information/data. Computer-readable media should not be construed or interpreted to include any propagating signals. A computer-readable medium of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

The subject invention includes, but is not limited to, the following exemplified embodiments.

Embodiment 1

A method of performing nanometer-scale microscopy on a sample, the method comprising:
i) providing the sample to an imaging system comprising a graphene layer, wherein the sample is disposed over the graphene layer;
ii) exciting a plurality of graphene plasmons (GPs) in the graphene layer as an illumination source for imaging the sample; and
iii) capturing an image of the sample using the GPs as the illumination source.

Embodiment 2

The method according to embodiment 1, wherein the imaging system further comprises a lens,
wherein the sample is disposed between the graphene layer and the lens, and
wherein capturing the image of the sample is performed by the lens.

Embodiment 3

The method according to embodiment 2, wherein the lens is an objective lens.

Embodiment 4

The method according to any of embodiments 1-3, wherein the imaging system further comprises a dielectric layer disposed on the graphene layer, such that the sample is disposed on the dielectric layer.

Embodiment 5

The method according to embodiment 4, wherein the dielectric layer has a thickness that is set or tuned to optimize the imaging result based on a desired result.

Embodiment 6

The method according to any of embodiments 4-5, wherein the graphene layer is in direct physical contact with (a lower surface of) the dielectric layer.

Embodiment 7

The method according to any of embodiments 4-6, wherein, during the steps of exciting the plurality of GPs and capturing the image of the sample, the sample is in direct physical contact with (an upper surface of) the dielectric layer.

Embodiment 8

The method according to any of embodiments 1-7, wherein the imaging system further comprises a substrate on which the graphene layer is disposed.

Embodiment 9

The method according to embodiment 8, wherein the substrate comprises dielectric gratings therein.

Embodiment 10

The method according to embodiment 9, wherein the dielectric gratings form a circle around a portion of the substrate over which the sample is disposed during the steps of exciting the plurality of GPs and capturing the image of the sample.

Embodiment 11

The method according to any of embodiments 8-10, wherein the graphene layer is in direct physical contact with (an upper surface of) the substrate.

Embodiment 12

The method according to any of embodiments 1-11, wherein the plurality of GPs is two GPs.

Embodiment 13

The method according to any of embodiments 1-12, wherein exciting the plurality of GPs comprises using a plurality of laser pulses to irradiate (the) dielectric gratings of (the substrate of) the imaging system to excite GPs.

Embodiment 14

The method according to embodiment 13, wherein exciting the plurality of GPs comprises using two laser pulses to excite two GPs.

Embodiment 15

The method according to any of embodiments 1-14, wherein steps ii) and iii) are performed multiple times to obtain a plurality of images that can be used to construct a master image of the sample.

Embodiment 16

The method according to any of embodiments 13-15, wherein each laser pulse has a duration in a range of from 1 nanosecond (ns) to 9 ns.

Embodiment 17

The method according to any of embodiments 13-15, wherein each laser pulse has a duration of 1 ns.

Embodiment 18

The method according to any of embodiments 13-17, wherein the separation between consecutive pulses is in a range of from 10 ns to 99 ns.

Embodiment 19

The method according to any of embodiments 13-17, wherein the separation between consecutive pulses is 30 ns.

Embodiment 20

The method according to any of embodiments 1-19, wherein a graphene charge carrier mobility of the graphene layer is in a range of from $10^4$ cm$^2$V$^{-1}$s$^{-1}$ to $10^6$ cm$^2$V$^{-1}$s$^{-1}$.

Embodiment 21

The method according to any of embodiments 1-19, wherein a graphene charge carrier mobility of the graphene layer is on the order of $10^4$ cm$^2$V$^{-1}$s$^{-1}$.

Embodiment 22

The method according to any of embodiments 1-19, wherein a graphene charge carrier mobility of the graphene layer is on the order of $10^5$ cm$^2$V$^{-1}$s$^{-1}$.

Embodiment 23

The method according to any of embodiments 1-19, wherein a graphene charge carrier mobility of the graphene layer is on the order of $10^6$ cm$^2$V$^{-1}$s$^{-1}$.

Embodiment 24

The method according to any of embodiments 1-19, wherein a graphene charge carrier mobility of the graphene layer is $10^4$ cm$^2$V$^{-1}$s$^{-1}$.

Embodiment 25

The method according to any of embodiments 1-19, wherein a graphene charge carrier mobility of the graphene layer is $10^5$ cm$^2$V$^{-1}$s$^{-1}$.

Embodiment 26

The method according to any of embodiments 1-19, wherein a graphene charge carrier mobility of the graphene layer is $10^6$ cm$^2$V$^{-1}$s$^{-1}$.

Embodiment 27

The method according to any of embodiments 1-26, wherein each GP of the plurality of excited GPs has the same wave number and a different propagation direction as all other excited GPs.

Embodiment 28

The method according to any of embodiments 1-27, wherein the plurality of excited GPs construct a periodic pattern in one dimension.

Embodiment 29

The method according to any of embodiments 1-28, wherein each GP of the plurality of excited GPs propagates and is reflected by (the) dielectric gratings of (the substrate of) the imaging system, thereby affecting a field pattern.

Embodiment 30

The method according to any of embodiments 1-29, wherein the graphene layer is a graphene monolayer.

Embodiment 31

A system performing nanometer-scale microscopy on a sample, the system comprising:
a substrate;
a graphene layer disposed on the substrate;
a dielectric layer disposed on the graphene layer and configured to have the sample disposed thereon; and
a lens positioned above the dielectric layer,
wherein the system is configured to perform imaging by exciting a plurality of graphene plasmons (GPs) in the graphene layer as an illumination source for imaging the sample, and using the lens to capture an image of the sample using the GPs as the illumination source.

Embodiment 32

The system according to embodiment 31, wherein the lens is an objective lens.

Embodiment 33

The system according to any of embodiments 31-32, wherein the dielectric layer has a thickness that is set or tuned to optimize the imaging result based on a desired result.

Embodiment 34

The system according to any of embodiments 31-33, wherein the graphene layer is in direct physical contact with (a lower surface of) the dielectric layer.

Embodiment 35

The system according to any of embodiments 31-34, wherein the system is configured such that, during use, the sample is in direct physical contact with (an upper surface of) the dielectric layer.

Embodiment 36

The system according to any of embodiments 31-35, wherein the substrate comprises dielectric gratings therein.

Embodiment 37

The system according to embodiment 36, wherein the dielectric gratings form a circle around a portion of the substrate over which the sample is disposed during use of the system.

Embodiment 38

The system according to any of embodiments 31-37, wherein the graphene layer is in direct physical contact with (an upper surface of) the substrate.

Embodiment 39

The system according to any of embodiments 31-38, wherein the plurality of GPs is two GPs.

Embodiment 40

The system according to any of embodiments 31-39, further comprising a laser, wherein exciting the plurality of GPs comprises using a plurality of laser pulses from the laser to irradiate (the) dielectric gratings of the substrate to excite GPs.

Embodiment 41

The system according to embodiment 41, wherein exciting the plurality of GPs comprises using two laser pulses to excite two GPs.

Embodiment 42

The system according to any of embodiments 31-41, wherein the system is configured to excite the plurality of GP and capture the image using the GPs as the illumination source multiple times to obtain a plurality of images that can be used to construct a master image of the sample.

Embodiment 43

The system according to any of embodiments 40-42, wherein each laser pulse has a duration in a range of from 1 nanosecond (ns) to 9 ns.

Embodiment 44

The system according to any of embodiments 40-42, wherein each laser pulse has a duration of 1 ns.

Embodiment 45

The system according to any of embodiments 40-44, wherein the separation between consecutive pulses is in a range of from 10 ns to 99 ns.

Embodiment 46

The system according to any of embodiments 40-44, wherein the separation between consecutive pulses is 30 ns.

Embodiment 47

The system according to any of embodiments 31-46, wherein a graphene charge carrier mobility of the graphene layer is in a range of from $10^4$ $cm^2V^{-1}s^{-1}$ to $10^6$ $cm^2V^{-1}s^{-1}$.

Embodiment 48

The system according to any of embodiments 31-46, wherein a graphene charge carrier mobility of the graphene layer is on the order of $10^4$ $cm^2V^{-1}s^{-1}$.

Embodiment 49

The system according to any of embodiments 31-46, wherein a graphene charge carrier mobility of the graphene layer is on the order of $10^5$ $cm^2V^{-1}s^{-1}$.

Embodiment 50

The system according to any of embodiments 31-46, wherein a graphene charge carrier mobility of the graphene layer is on the order of $10^6$ $cm^2V^{-1}s^{-1}$.

Embodiment 51

The system according to any of embodiments 31-46, wherein a graphene charge carrier mobility of the graphene layer is $10^4$ $cm^2V^{-1}s^{-1}$.

Embodiment 52

The system according to any of embodiments 31-46, wherein a graphene charge carrier mobility of the graphene layer is $10^5$ $cm^2V^{-1}s^{-1}$.

Embodiment 53

The system according to any of embodiments 31-46, wherein a graphene charge carrier mobility of the graphene layer is $10^6$ $cm^2V^{-1}s^{-1}$.

Embodiment 54

The system according to any of embodiments 31-53, wherein each GP of the plurality of excited GPs has the same wave number and a different propagation direction as all other excited GPs.

Embodiment 55

The system according to any of embodiments 31-54, wherein the plurality of excited GPs construct a periodic pattern in one dimension.

Embodiment 56

The system according to any of embodiments 31-55, wherein each GP of the plurality of excited GPs propagates and is reflected by (the) dielectric gratings of the substrate, thereby affecting a field pattern.

Embodiment 57

The system according to any of embodiments 31-56, wherein the graphene layer is a graphene monolayer.

A greater understanding of the present invention and of its many advantages may be had from the following examples, given by way of illustration. The following examples are illustrative of some of the methods, applications, embodiments and variants of the present invention. They are, of course, not to be considered as limiting the invention. Numerous changes and modifications can be made with respect to the invention.

Example 1

Figure 3A:
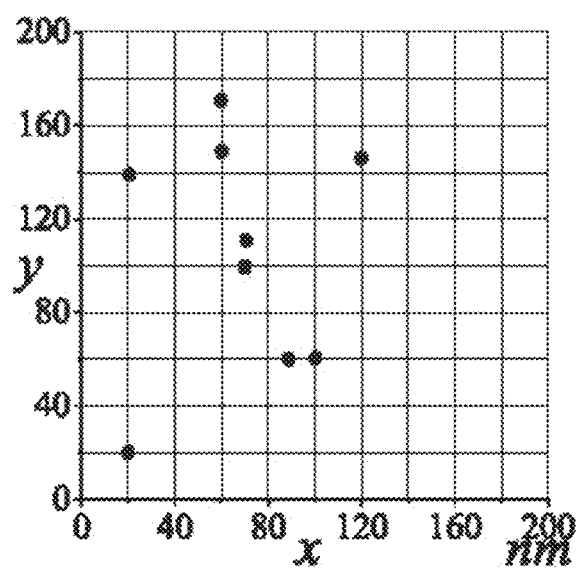
FIG. 3A shows atom distribution for an imaging simulation.
Figure 3B:
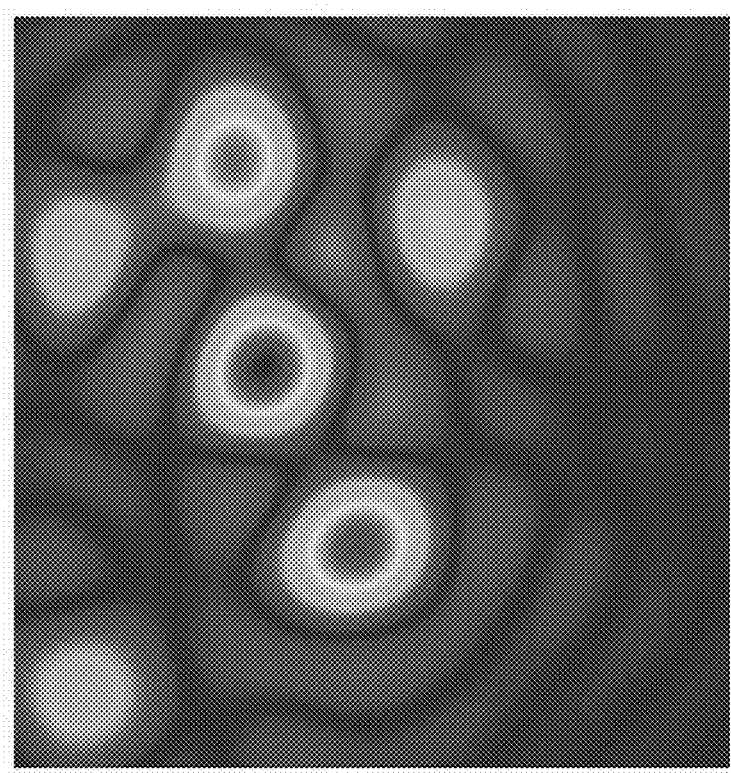
FIG. 3B shows a simulated image using a method of an embodiment of the subject invention, with $E_F=0.4$, $\hbar\omega=0.2$ eV, $\varepsilon_1=2$, and $\varepsilon_2=2$, where Re($k_{gp}$)=68.5 $k_D$.
Figure 3C:
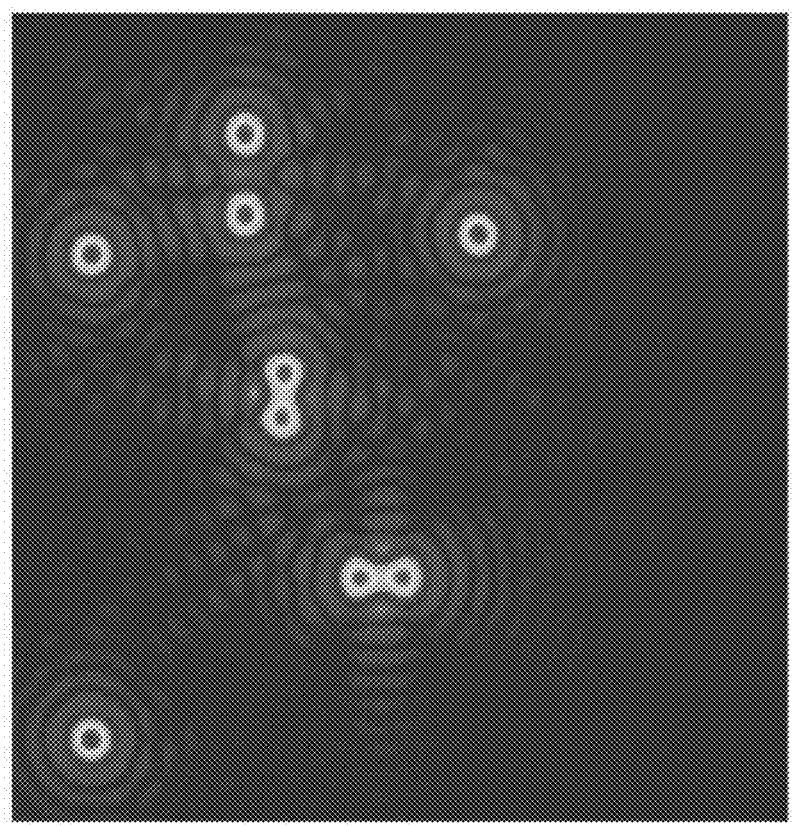
FIG. 3C shows a simulated image using a method of an embodiment of the subject invention, with $E_F=0.6$, $\hbar\omega=0.4$ eV, $\varepsilon_1=3$, where Re($k_{gp}$)=137 $k_c$.

A sample similar to that in Heintzmann et al. (*J. Opt. Soc. Am. A.*, 19, 1599, 2002) and Gustafsson (*Proc. Natl. Acad. Sci.*, USA, 102, 13081, 2005) was analyzed using a system as described herein. Knowing all the Fourier information, an image of the sample was reconstructed. FIGS. 3A, 3B, and 3C demonstrate the image simulations under different parameters. In the simulations, first, Fourier transformation were performed on the atom distribution function to get the Fourier information $f(k_x,k_y)$; second, inverse Fourier transformation of $f(k_x,k_y)$ were performed within $k_x^2+k_y^2 \leq 2 k_{gp}+\kappa$. Then, high-resolution images were obtained. Here, it was assumed that NA=1. FIG. 3B shows a resolution increase of 68.5 times, and FIG. 3C shows a resolution increase of 137 times, thereby proving that nanometer-scale microscopy can be achieved using a mid-infrared field.

Figure 4:
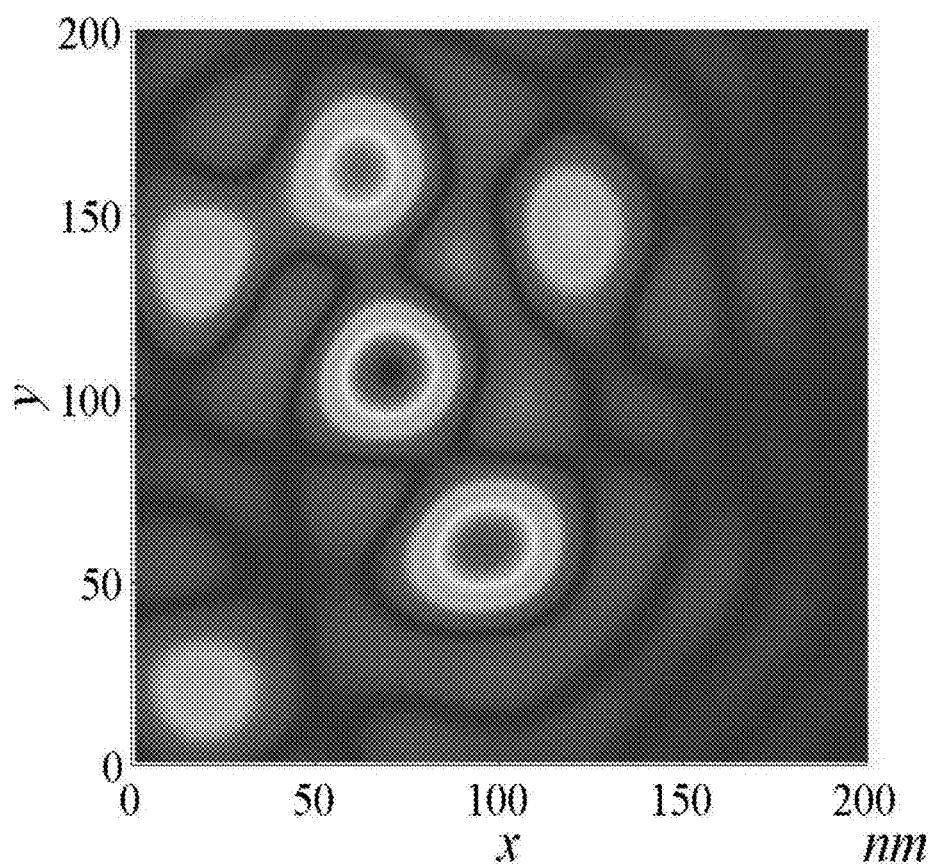
FIG. 4 shows a simulated image using the same conditions as in FIG. 3B, but considering loss. At the origin point, the two GPs have the same intensity.

The influence of the dissipation of the GPs on the results has not been considered above. As shown in FIG. 1C, if $\mu=10^4$ cm$^2$V$^{-1}$s$^{-1}$, only the area near the spot where the two plasmons have the same amplitude can the illumination pattern be approximated as sinusoidal. At the position away from the spot, the field irradiated on the sample can be considered as the sum of a plane wave and a sinusoidal pattern. Then, the observed image has two contributions. The information in the sinusoidal pattern field is contained in all three circles in FIG. 2A, but the contribution due to the plane field is contained only in the circle located at the origin. Thus, ignoring the plane-wave contribution may lead to an error. However, this effect has a small influence on the results discussed herein. For example, in FIG. 4, the reconstructed image for the case where $\mu=10^4$ cm$^2$V$^{-1}$s$^{-1}$ was simulated. The Fourier components in Equation (4) are revised to $$\iint F(x,y)e^{-2\gamma_y y'}e^{-i(k_x-k_1)x}e^{-ik_y y'}dx\,dy,$$
$$\iint F(x,y)e^{-2\gamma_y y'}e^{-i(k_x+k_1)x}e^{-ik_y y'}dx\,dy,$$
$$\text{and } \iint F(x,y)e^{-2\gamma_y y'}(e^{-\gamma_x x}+e^{\gamma_x x})e^{-ik_x x}e^{-ik_y y'}dxdy.$$

Here, $\gamma_x$ and $\gamma_y$ are the imaginary parts of the plasmon wave vector along the x- and y-directions, respectively, with $\sqrt{\gamma_x^2+\gamma_y^2}=\text{Im}(k_{gp})$. These components can be obtained if $\gamma_x/\text{Re}(k_{gp}) \ll 1$. In this example, the Fourier transformation of the sample distribution is the coherent summation of the transformations of the positions of separated atoms. The loss can affect the relative ratio between the amplitudes of the Fourier components of a single atom, which induces the image of an atom not to be a circular spot. In experiment, the Fourier-transformation components in the circle located at the origin with radius K can be obtained exactly by a conventional microscopy process. If two observations are performed with opposite y directions on the sample, the average Fourier components outside of the circle located at the origin with radius K are $$\iint F(x,y)(e^{-2\gamma_y y'}/2+e^{2\gamma_y y'}/2)e^{-i(k_x-k_1)x}e^{-ik_y y'}dx\,dy \text{ and}$$

$$\iint F(x,y)(e^{-2\gamma_y y'}/2+e^{2\gamma_y y'}/2)e^{-i(k_x-k_1)x}e^{-ik_y y'}dx\,dy.$$

It is assumed that when the maximum loss enlarged Fourier transformation amplitude is smaller than 1.2 times the original value, the effect of loss can be neglected. This means $e^{-2\gamma_y y'}/2+e^{2\gamma_y y'}/2<1.2$. Thus, the sample size should be smaller than $2.5\alpha\mu E_F^2[\hbar(\varepsilon_1+\varepsilon_2)k_0e\upsilon_F^2]$. It follows, on comparing FIG. 4 with FIG. 3B, that the influence of the loss is very small.

Of course, if the size of the sample is quite big compared to the GP wavelength, the dissipation effect discussed above cannot be neglected. To overcome this problem, another energy level $|c\rangle$ of the sample atom can be used, which is shown in FIG. 5A. After the atom is excited to state $|e\rangle$, a pulse that is incident normal to the sample plane can be used to drive the atom from $|e\rangle$ to $|c\rangle$. The pattern of the GPs in the pulse domain can be considered to be sinusoidal. The field of the pulse section is Gaussian. As a result, after the pulse, the population of $|c\rangle$ in the pulse domain can present a shape with a maximum at the pulse center and can decrease away from the center. The distribution can be described as G(x,y) depending on the field intensity and the decay rates of the atomic levels with a nonzero result only in the Gaussian pulse domain. The image result is equal to the case of replacing F(x,y) in Equation (2) with F(x, y)G(x,y).

The atom at the position can be distinguished with G(x,y) a little bigger than 0, which is done in order to overcome the noise. In the imaging process, the photons emitted from $|c\rangle$ to $|d\rangle$ with frequency $\omega_{cd}$ can be used for imaging. The probability to get a photon at frequency $\omega_{cd}$ is about $\Gamma_0/(\Gamma_0+\Gamma_{ce})$. Controlling the position of the Gaussian pulse, every time, the image can be reconstructed in the range of the pulse width. Changing the positions of the GPs and the Gaussian pulse, the entire sample can be imaged. Additionally, $\omega_{cd}>\omega_{eg}$ means a larger K and can lead to a faster imaging process.

With recent progress in the fabrication and manipulation of graphene, a mobility as large as $\mu=10^5$ cm$^2$V$^{-1}$s$^{-1}$ or $\mu=10^6$ cm$^2$V$^{-1}$s$^{-1}$ can be achieved. This results in a lower loss. Referring to FIG. 1C, the field intensity is plotted with $\mu=10^5$ cm$^2$V$^{-1}$s$^{-1}$; an almost perfect sinusoidal field pattern can be obtained, leading to higher precision.

Another potential issue is that the fluorescence photons may be absorbed by the graphene due to the strong coupling between the GPs and the emitters. To address this issue, choosing the thickness h of the dielectric slab is important. The coupling strength between the emitter and the plasmon decreases exponentially as the distance to the graphene plane increases (see also Koppens et al. (*Nano Lett.*, 11, 3370, 2011, which is hereby incorporated herein by reference in its entirety). Therefore, a relatively large h can be chosen to result in most of the photons being collected by the lens (e.g., objective lens). Meanwhile, the intensity of the illumination plasmons decreases rapidly as the dielectric layer thickness h increases. Therefore, the intensity of the illumination plasmons can be increased to make sure the field on the sample is strong enough to drive the atom. The thickness of the upper dielectric layer (or dielectric slab) can therefore be determined or tuned based on the desired result.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

E. Betzig, G. H. Patterson, R. Sougrat, 0. W. Lindwasser, S. Olenych, J. S. Bonifacino, M. W. Davidson, J. L. Schwartz, and H. F. Hess, Science 313, 1642 (2006).

C. Hettich, C. Schmitt, J. Zitzmann, S. Kuhn, I. Gerhardt, and V. Sandoghdar, Science 298, 385 (2002).

Z. Y. Liao, M. Al-Amri, and M. S. Zubairy, Phys. Rev. A 85, 023810 (2012).

J. T. Chang, J. Evers, M. O. Scully, and M. S. Zubairy, Phys. Rev. A 73 031803 (R) (2006)

J. T. Chang, J. Evers, and M. S. Zubairy, Phys. Rev(A 74, 04382; •} (2006).

S. Qamar, J. Evers, and M. S. Zubairy, Phys. Rev A 79, 043814 (2009).

H. B. Li, V. A. Sautenkov, M. M. Kash, A. V. Sokolov, G. R. Welch, Y. V. Rostovtsev, M. S. Zubairy, and M. O. Scully, Phys. Rev. A 78, 013803 (2008).

M. J. Rust, M. Bates, and X. Zhuang, Nat. Methods 3, 793 (2006).

Z. Liu, H. Lee, Y. Xiong, C. Sun, and X. Zhang, Science 315, 1686 (2007).

V. Westphal and S. W. Hell, Phys. Rev Lett. 94, 143903 (2005).

D. Wildanger, J. R. Maze, and S. W. Hell, Phys. Rev. Lett 107, 17601 2011.

T. A. Klar, S. Jakobs, N. Dyba, A. Egner, and S. W. Hell, Proc. Science Natl. Acad. Sci. USA 97, 8206 (2000).

M. G. L. Gustafsson, J Microsoft, 198, 82 (2000).

J. T. Frohn, H. F. Knapp, and A. Stemmer, Proc. Natl. Acad. Sci. USA 97, 7232(2000).

R. Heintzmann, T. M. Jovin, and C. Cremer, J. Opt. Soc. Am. A USA 97, 1599 (2002).

M. G. L. Gustafsson, Proc. Natl. Acad. Sci USA 102, 13081 (2005).

F. Wei and Z. Liu, Nano Lett. 10, 2531 (2010).

A. K. Geim and K. S. Novoselov, Nature Matter, 6 183, (2007).

A. H. Castro Neto, F. Guinea, N. M. R. Peres, K. S. Novoselov, and A. K. Geim, Rev. Mod. Phys. 81, 109 (2009).

R. R. Nair, P. Blake, A. N. Grigorenko, K. S. Novoselov, T. J. Booth, T. Stauber, N. M. R. Peres, and A. K. Geim, Science 320, 1308 (2008).

J. Chen, M. Badioli, P. Alonso-Gonzalez, S. Thongrattanasiri, F. Huth, J. Osmond, M. Spasenovic, A. Centeno, A. Pesquera, P. Godignon, A. Z. Elorza, N. Camara, F. J. Garcia de Abajo, R. Hillenbrand, and F. H. L. Koppens, Nature 487, 77 (2012).

Z. Fei, A. S. Rodin, G. O. Andreev, W. Bao, A. S. McLeod, M. Wagner, L. M. Zhang, Z. Zhao, M. Thiemens, G. Dominguez, M. M. Fogler, A. H. Castro Neto, C. N. Lau, F. Keilmann, and D. N. Basov, Nature 487, 82 (2012).

Z. Fang, S. Thongrattanasiri, A. Schlather, Z. Liu, L. Ma, Y. Wang, P. M. Ajayan, P. Nordlander, N.J. Halas, and F. J. Garcia de Abajo, ACS Nano 7, 2388 (2013).

T. Low and P. Avoruis, ACS Nano 8, 1086 (2014).

L. Ju, B. Geng, J. Horng, C. Girit, M. Martin, Z. Hao, H. A. Bechtel, X. Liang, A. Zettl, Y. R. Shen, and F. Wang, Natl. Nanotechnology, 6, 630 (2011).

M. Gullans, D. E. Chang, F. H. L. Koppens, F. J. Garciade Abajo, and M. D. Lukin, Phys. Rev. Lett. 111, 247401 (2013).

A. N. Grigorenko, M. Polini, and K. S. Novoselov, Nat. Photonics, 6, 749 (2012). A. Vakil and N. Engheta, Science 332, 1291 (2011).

T. R. Zhan, F. Y. Zhao, X. H. Hu, X. H. Liu, and J. Zi, Phys Rev. B 86, 165416 (2012).

B. Wunsch, T. Stauber, F. Sols, and F. Guinea, New J. Phy. 8, 318 (2006).

E. H. Hwang and S. Das Sarma, Phys. Rev. B 75, 205418 (2007).

S. A. Mikhailov and K. Ziegler, Phys. Rev. Lett. 99, 016083, (2007).

M. Jablan, H. Buljan, and M. SoljaciC, Phys. Rev. B 80, 245435 (2009)

F. H. L. Koppens, D. E. Chang, and M. Soljacc, Nano Lett. 11, 3370 (2011).

X. H. Yao, M. Tokman, and A. Belyanin, Phys. Rev. Lett. 112, 055501 (2014)

B. Wang, X. Zhang, F. J. Garcia-Vidal, X. C. Yuan, and J. H. Teng, Phys. Rev. Lett. 109, 073901 (2012).

F. Balzarotti and F. D. Stefani, ACS Nano 6, 4580 (2012).

B. Gjonaj, J. Aulbach, P. M. Johnson, A. P. Mosk, L. Kuipers, and A. Lagendijk, Phys. Rev. Lett. 110, 266804 (2013).

What is claimed is:

1. A method of performing nanometer-scale microscopy on a sample, the method comprising:
   i) providing the sample to an imaging system comprising a graphene layer, wherein the sample is disposed over the graphene layer;
   ii) exciting a plurality of graphene plasmons (GPs) in the graphene layer as an illumination source for imaging the sample; and
   iii) capturing an image of the sample using the GPs as the illumination source,
   wherein the imaging system further comprises a substrate on which the graphene layer is disposed, the substrate comprising a plurality of dielectric gratings therein,
   wherein the imaging system further comprises a dielectric layer disposed on the graphene layer, such that the sample is disposed on the dielectric layer,
   wherein the imaging system further comprises a lens,
   wherein the sample is disposed between the graphene layer and the lens,
   wherein capturing the image of the sample is performed by the lens,
   wherein the dielectric gratings form a circle around a portion of the substrate over which the sample is disposed during the steps of exciting the plurality of GPs and capturing the image of the sample,
   wherein the graphene layer is in direct physical contact with an upper surface of the substrate,
   wherein exciting the plurality of GPs comprises using a plurality of laser pulses to irradiate the dielectric gratings of the substrate to excite GPs,
   wherein each laser pulse has a duration in a range of from 1 nanosecond (ns) to 9 ns, and
   wherein the separation between consecutive pulses is in a range of from 10 ns to 99 ns.

2. The method according to claim 1, wherein the dielectric layer has a thickness that is set or tuned to optimize the imaging result based on a desired result.

3. The method according to claim 1, wherein the graphene layer is in direct physical contact with a lower surface of the dielectric layer, and
   wherein, during the steps of exciting the plurality of GPs and capturing the image of the sample, the sample is in direct physical contact with an upper surface of the dielectric layer.

4. The method according to claim 1, wherein exciting the plurality of GPs comprises using two laser pulses to excite two GPs.

5. The method according to claim 1, wherein steps ii) and iii) are performed multiple times to obtain a plurality of images that can be used to construct a master image of the sample.

6. The method according to claim 1, wherein the graphene layer is a graphene monolayer.

7. A system for performing nanometer-scale microscopy on a sample, the system comprising:
   a substrate comprising a plurality of dielectric gratings therein;
   a graphene layer disposed on the substrate;
   a dielectric layer disposed on the graphene layer and configured to have the sample disposed thereon; and
   a lens positioned above the dielectric layer,
   wherein the system is configured to perform imaging by exciting a plurality of graphene plasmons (GPs) in the graphene layer as an illumination source for imaging the sample, and using the lens to capture an image of the sample using the GPs as the illumination source, wherein the graphene layer is in direct physical contact with a lower surface of the dielectric layer, wherein the system is configured such that, during use, the sample is in direct physical contact with an upper surface of the dielectric layer, wherein the dielectric gratings form a circle around a portion of die substrate over Which the sample is disposed during use of the system, wherein the graphene layer is in direct physical contact with an upper surface of the substrate, wherein the system further comprises a laser, wherein exciting the plurality of GPs comprises using a plurality of laser pulses from the laser to irradiate the dielectric gratings of the substrate to excite GPs, wherein each laser pulse has a duration in a range of from 1 nanosecond (ns) to 9 ns, and wherein the separation between consecutive pulses is in a range of from 10 ns to 99 ns.

8. The system according to claim 7, wherein the dielectric layer has a thickness that is set or tuned to optimize the imaging result based on a desired result.

9. The system according to claim 7, wherein the system is configured to excite the plurality of GP and capture the image using the GPs as the illumination source multiple times to obtain a plurality of images that can be used to construct a master image of the sample.

10. The system according to claim 7, wherein each GP of the plurality of excited GPs has the same wave number and a different propagation direction as all other excited GPs, wherein the plurality of excited GPs construct a periodic pattern in one dimension, and wherein each GP of the plurality of excited GPs propagates and is reflected by dielectric gratings of the substrate, thereby affecting a field pattern.

11. The system according to claim 7, wherein the graphene layer is a graphene monolayer.

* * * * *